United States Patent [19]

Baum et al.

[11] 4,022,811
[45] May 10, 1977

[54] PREPARATION OF ALKYL PERBROMATES
[75] Inventors: Kurt Baum, Pasadena, Calif.; Charles D. Beard, Yorktown Heights, N.Y.; Vitautas Grakaukas, Arcadia, Calif.
[73] Assignee: The United States of America as represented by the Secretary of the Navy, Washington, D.C.
[22] Filed: Jan. 21, 1976
[21] Appl. No.: 650,829
[52] U.S. Cl. .......................... 260/453 RX; 423/476
[51] Int. Cl.² .......................................... C07C 71/00
[58] Field of Search ............... 260/453 RZ, 453 RX

[56] References Cited
OTHER PUBLICATIONS

Baum et al., J. A. Chem. Soc., vol. 96, (1974), pp. 3233–3236.

Primary Examiner—Delbert R. Phillips
Attorney, Agent, or Firm—R. S. Sciascia; Philip Schneider; Thomas McDonnell

[57] ABSTRACT

Derivatives of perbromic acid of the formula: $XBrO_4$ wherein X is Ag, $(CH_3)_2CH$, or $(CH_3)_2C_2H_3$ prepared by a synthesis of silver perbromate through the reaction of dilute aqueous perbromic acid with silver oxide at a temperature from 0° to 50° C, followed by a removal of water and by a synthesis of isopropyl or isobutyl perbromate through the reaction of anhydrous silver perbromate suspended in a fluid selected from the class consisting of carbon tetrachloride, cyclohexane, and 1,1,2-trichlorotrifluoroethane with an alkyl bromide at a temperature from −25° to 0° C. Isopropyl and isobutyl perbromates are useful as oxidizing agents for alcohols.

3 Claims, No Drawings

PREPARATION OF ALKYL PERBROMATES

BACKGROUND OF THE INVENTION

This invention pertains generally to organic synthesis and in particularly to the synthesis of derivatives of the inert and unstable perbromic acid.

The alkali metal and ammonium salts of perbromic acids have been prepared. Various attempts have been made without success to prepare esters and other salts of this acid. Attempts to prepare alkyl perbromates by treating alkyl iodides with suspensions of silver perbromate in carbon tetrachloride at 0° C have not been successful. An immediate reaction takes place, producing elemental iodine but no simple organic compounds.

An attractive method for the synthesis of alkyl perbromates would be the reaction of dibromine heptoxide with alcohols, since the corresponding reaction of dichlorine heptoxide is a convenient source of alkyl perchlorates. Dibromine heptoxide, however, has not been prepared, and attempts to dehydrate aqueous perbromic acid at room temperature results in autocatalytic decomposition after the dihydrate stage. Another possible method would be the reaction of silver perbromate with an alkyl bromide, but silver perbromate has not been prepared. In fact the silver ion has been reported to catalyze the decomposition of 6 M perbromic acid.

SUMMARY OF THE INVENTION

It is therefore an object of this invention to provide methods of preparation for silver perbromate and lower alkyl perbromates.

Another object of this invention is to provide strong oxidizing agents for alcohols.

These and other objects are achieved by the preparation of silver perbromate from the reaction of a 0.2 to 0.7 M solution of perbromic acid with silver oxide at a temperature from 0° to 50° C, followed by removal of water from the product thereby avoiding an extensive decomposition of perbromic acid and by the preparation of lower alkyl perbromates through reaction of silver perbromate with a lower alkyl bromide at a temperature from −25° to 0° C.

DETAILED DESCRIPTION OF THE INVENTION

Perbromic acid may be prepared according to the method in Appelman, E. H., *Inorganic Synthesis*, 13, 1 (1972), using elemental fluorine to oxidize the bromate. For the practice of this invention the concentration of the acid is from 0.2M to 0.7M with 0.4M to 0.6M preferred.

To prepare silver perbromate, perbromic acid is stirred with the stoichiometric amount of silver oxide at a temperature from 0° to 50° C with 10° to 25° C preferred. The reaction proceeds, accordingly, $$Ag_2O + 2\ HBrO_4 \rightarrow 2\ AgBrO_4 + H_2O$$

The order of addition of the reactants is not critical and an excess of either reactant does interfere with the synthesis. The stirring should be sufficient to ensure a uniform distribution of the reactants.

The end point can be determined by nmr analysis. After the reaction is completed the bulk of the water is removed by, e.g. vacuum and the concentrate is dried by azetroping with benzene or the like. The product, which is soluble in benzene, is precipitated by the addition of hexane, heptane, or the like.

Silver perbromate was identified by analysis for silver, using sodium chloride. It reacted with saturated aqueous hydrobromic acid to give the theoretical amount of bromine, determined iodometrically, using the conditions reported for the analysis of perbromic acid. The appearance and solubility properties of silver perbromate are similar to those of anhydrous silver perchlorate; it is a white hygroscopic solid, soluble in benzene and insoluble in saturated hydrocarbons. The material was unchanged in several months at ambient temperature.

The preparation of the lower alkyl perbromates proceeds as follows:

$$XBr + AgBrO_4 \rightarrow (CH_3)_2CHOBrO_3 + AgBr$$

wherein $X = (CH_3)_2CH$ or $(CH_3)_2C_2H_3$. This reaction does not proceed for simple primary alkyl bromides.

Preferably in carrying out this reaction, stoichiometric amounts of an alkyl bromide and anhydrous silver perbromate suspended in an inert fluid, e.g., carbon tetrachloride, cyclohexane, or 1,1,2-trichlorotrifluoroethane are added together in any order. The amount of the inert fluid should be such that the product concentration does not exceed 15% by weight and preferably is 6% by weight. The mixture is stirred sufficiently to provide a uniform distribution of the reactants and the reaction is carried out at a temperature from −25° to 0° C with −25° to −10° C most preferred. An excess of either reactant would not hinder the reaction.

In the following examples, nmr spectra were recorded with a Varian T-60 spectrometer and the ir spectra were recorded with a Perkin-Elmer 700 spectrometer. Adequate safety shields were used and tongs were used for manipulations in the gram-scale reactions. It is to be understood that these examples are given by way of illustration and are not meant to limit this specification or the claims to follow in any manner.

EXAMPLE I

Preparation of Silver Perbromate

Silver oxide (5.80 g, 0.025 mol) was added in portions, with stirring, to 100 ml of 0.5 M perbromic acid. The mixture was stirred with a magnetic stirrer for 2 hours at ambient temperature (23° C) and was then filtered through sintered glass. The bulk of water was removed from the filtrate under vacuum, and 100 ml of benzene was added. The remaining water was removed by azeotropic distillation using a Dean-Stark trap. The resulting benzene solution was filtered hot. When the solution was cooled to room temperature, 100 ml of hexane was added. The solvent was decanted from the precipitated salt, and the salt was dried briefly at 25° (0.05 mm), and was then heated with a 70° bath at 0.05 mm for 6 hours to remove adsorbed solvent. The product, 11.1 g (88%), was a white, hygroscopic, crystalline solid.

EXAMPLE II

Preparation of Isopropyl Perbromate

A solution of 0.123 g (1.0 mmol) of isopropyl bromide in 1 ml of carbon tetrachloride was added dropwise, with stirring by a magnetic stirrer, to a suspension of 0.252 g (1.0 mmol) of silver perbromate in 4 ml of carbon tetrachloride, maintained at −20° C by means of a carbon tetrachloride dry ice slush bath. The reaction mixture was kept at −20° C for 15 minutes. The silver bromide was removed by filtration, giving a pale yellow solution. The same procedure was used to prepare solutions in the solvents cyclohexane and 1,2,2-trichlorotrifluoroethane: nmr ($CCl_4$) δ 5.17 (septet, 1 H, J = 6 Hz, $CHOBrO_3$) and 1.52 ppm (d, 6 H, J = 6 Hz, $CH_3$); ir ($CCl_4$) 3010 (m), 1460 (m), 1390 (m), 1190 (w), 1150 (m), 1100 (s), 945 (vs), 900 (m), and 860 $cm^{-1}$ (m); ir (cyclohexane) 790 $cm^{-1}$ (vs). The yield of isopropyl perbromate was 95%, determined by nmr integration using chlorobenzene as a quantitative internal standard. The only impurity detected was 1% of acetone. The decomposition of isopropyl perbromate solutions was monitored similarly by nmr. The solutions showed no decomposition within several hours at −20° C. At ambient temperature, the compound decomposed with a half-life of about 30 minutes to give acetone as the only product detectable by nmr. The yield of acetone was 90% in 24 hours. The solution became red-orange in color.

EXAMPLE III

Reaction of Isopropyl Perbromate with Ethyl Iodide

A solution of isopropyl perbromate in carbon tetrachloride was mixed with ethyl iodide at −20° C, iodine was liberated rapidly.

The decomposition of isopropyl perbromate at room temperature indicates that perbromates are intrinsically much stronger oxidizing agents than perchlorates because a similar decomposition is not observed with isopropyl perchlorate, even on prolonged storage. This conclusion is also consistent with the assumption of a high activation barrier for reduction of perbromate used to explain their inertness. This barrier is lowered because of the intramolecular nature of the oxidation-reduction reaction leading to the formation of acetone from isopropyl perbromate.

The reaction of isopropyl perbromate with ethyl iodide shows that the oxidizing properties of alkyl perbromates are incompatible with their preparation from alkyl iodides and silver perbromate. Again what is shown is the exceptional oxidizing strength of alkyl perbromates.

Obviously many modifications and variations of the present invention are possible in light of the above teachings. It is therefore to be understood that, within the scope of the appended claims, the invention may be practiced otherwise than as specifically described.

What is claimed and desired to be secured by Letters Patent of the United States is:

1. A composition of matter of the formula $XBrO_4$ wherein X = $(CH_3)_2CH$, and $(CH_3)_2C_2H_3$.

2. The composition of matter of claim 1 wherein X is $(CH_3)_2CH$.

3. The composition of matter of claim 1 wherein X is $(CH_3)_2C_2H_3$.

* * * * *